United States Patent [19]
Taylor

[11] Patent Number: 5,989,323
[45] Date of Patent: *Nov. 23, 1999

[54] AQUATIC ANTIFOULING COMPOSITIONS AND METHODS

[75] Inventor: Gordon T. Taylor, East Setauket, N.Y.

[73] Assignee: The Research Foundation of State University of New York, Stony Brook, N.Y.

[*] Notice: This patent is subject to a terminal disclaimer.

[21] Appl. No.: 08/956,800

[22] Filed: Oct. 23, 1997

Related U.S. Application Data

[63] Continuation-in-part of application No. 08/799,290, Feb. 13, 1997, Pat. No. 5,695,552, which is a continuation of application No. 08/164,328, Dec. 9, 1993, abandoned.

[51] Int. Cl.$^6$ .............................. A01N 63/00; A01N 25/00
[52] U.S. Cl. .................. 106/15.05; 422/6; 424/78.09; 424/93.7; 424/520; 424/538; 424/547; 427/384; 427/385.5; 427/393; 427/393.6; 427/397; 523/122; 523/177
[58] Field of Search ........................... 106/15.05; 422/6; 424/78.09, 93.7, 520, 538, 547; 427/384, 385.5, 393, 393.6, 397; 523/122, 177

[56] References Cited

U.S. PATENT DOCUMENTS

| | | | |
|---|---|---|---|
| 2,138,831 | 12/1938 | Brammer | 422/6 |
| 3,415,928 | 12/1968 | Nadal et al. | 424/195.1 |
| 3,441,439 | 4/1969 | Eagell | 134/37 |
| 4,259,269 | 3/1981 | Flowers | 261/151 |
| 4,313,827 | 2/1982 | Ratigan et al. | 210/136 |
| 4,328,638 | 5/1982 | Smithson | 424/708 |
| 4,556,486 | 12/1985 | Merket | 210/170 |
| 4,788,302 | 11/1988 | Costlow et al. | 106/15.05 |
| 4,818,413 | 4/1989 | Hoover et al. | 210/739 |
| 4,857,209 | 8/1989 | Lyons et al. | 210/755 |
| 5,008,075 | 4/1991 | Rufolo | 422/6 |
| 5,096,488 | 3/1992 | Stovicek | 106/18.32 |
| 5,116,407 | 5/1992 | Hunter et al. | 106/16 |
| 5,143,545 | 9/1992 | Stiffey et al. | 106/15.05 |
| 5,199,977 | 4/1993 | Yamamori et al. | 106/15.05 |

FOREIGN PATENT DOCUMENTS

| | | |
|---|---|---|
| 0556949 | 8/1993 | European Pat. Off. . |
| 0593135 | 4/1994 | European Pat. Off. . |
| 4252284 | 9/1992 | Japan . |
| 504903 | 5/1993 | Japan . |
| 5155873 | 6/1993 | Japan . |
| 5271009 | 10/1993 | Japan . |
| 2 159 056 | 11/1995 | United Kingdom . |
| 8901512 | 2/1989 | WIPO . |

OTHER PUBLICATIONS

Dilip de Silva et al., Three New Sesterterpenoid Antibiotics From the Marine Sponge *Luffariella Variablis,* Tetrahedon Letters, vol., 22, No. 33, pp. 3147–3150 (1981) No Month.
Nakatsu et al., Antimicrobial Constituents of Udotea Flabellum, The Journal of Organic Chemistry, vol. 46, No. 12, pp. 2435–2438 (1981) No Month.
Lindquist et al., Isolation and Structure Determination of Diazonmaides A and B, Unusual Cytotoxic Metabolites from the Marine Ascidian *Diazona chinensis,* J. Am. Chem. Soc. 113, pp. 2303–2304, (1991) No Month.
Keifer et al., Renillafoulins, Antifouling Dieterpenes from the Sea Pansy Renilla, J. Org. Chem., 51 pp. 4450–4454 (1986) No Month.
Teeyapant et al., Antibiotic and Cytotoxic Activity of Brominated Compounds from the Marine Sponge *Verongia aerophoba,* J. Biosci, 48 (11–12), pp. 939–945 (1993) No Month.
Wahl et al., Chemical Control of Bacterial Epibiosis on Ascidians, Marine Ecology Progress Series, vol. 110, pp. 45–57 (1994) No Month.
Bobzin et al., Diterpenes From the Pohnepeian Marine Sponge *Chelonaplysilla* SP, Journal of Natural Products, vol. 54, No. 1, pp. 225–232, Jan.–Feb. (1991).
Uriz et al., Relationships of Biological and Taxonomic Characteristics to Chemically Mediated Bioactivity in Mediterranean Littoral Sponges, Marine Biology, 113, pp. 287–297 (1992) No Month.
Minturn Wright, Antibiotic and Antifouling Properties of Marine Invertbrate Extracts: Comparative Aspects of Sponges and Gorgonians, Bioactivity Compounds From Marine Organisms, Thompson et al. eds., pp. 351–356 (1991) No Month.
D.J. Faulkner, Marine Natural Products, Natural Products Report, 4, pp. 539–576 (1986) No Month.
Chang et al., Antibiotic Substances Produced by a Marine Green Alga, *Dunaliella Promolecta,* Bioresource Technology, 44 (2) pp. 149–153 (1993) No Month.
Coll et al., The Application of Vacuum Liquid Chromatography to the Separation of Terpene Mixtures, Journal of Natural Products, vol. 49, No. 5, pp. 934–936 (1986) No Month.
Gerhart et al., Chemical Ecology and the Search for Marine Antifoulants, Journal of Chemical Ecology, vol. 14, No. 10, pp. 1905–1915 (1988) No Month.
Glombitza et al., Antibiotics from Algae XXXIII[1]: Phlorotannins of the Brown Alga *Minanthalia Elongaga* [2,3], Planta Medica, 51, pp. 42–46 (1984) No Month.
Matsunaga et al., Bioactive Marine Metabolites, VIII. Isolation of an Antimicrobial Blue Pigment from the Bryozoan Bugula Dentata, Experientia, 42, 84 (1986) No Month.
Paul J. Scheuer, Some Marine Ecological Phenomena: Chemical Basis and Biomedical Potential, Sciences, 248, pp. 173–177 (1990) No Month.

(List continued on next page.)

*Primary Examiner*—Anthony Green
*Attorney, Agent, or Firm*—Dilworth & Barrese

[57] ABSTRACT

Aquatic organism repellent agents are derived from algae, sponges, tunicates, bryozoans, echinoderms and coelenterates and prevent the attachment and accumulation of microscopic and macroscopic organisms to surfaces in aquatic environments. One or more of the agents may be incorporated into a carrier for release of the agent in the locus to be protected.

20 Claims, No Drawings

OTHER PUBLICATIONS

Sears et al., Antifouling Agents From Marine Sponge, Journal of Chemical Ecology, vol. 16, No. 3, pp. 791–799 (1990) No Month.
Dilip de Silva et al., Manoalide, An Antibiotic Sesterterpenoid From the Marine Sponge Luffariella Variabilis (Polejaeff), Tetrahedron Letters, vol. 21, pp. 1611–1614 (1980) No Month.
Davis et al., Epibiosis of Marine Algae and Benthic Invertebrates: Natural Products Chemistry and Other Mechanims Inhibiting Settlement and Overgrowth, Bioorganic Marine Chemistry, Springer–Verlag Berlin, 3, pp. 85–114 (1987) No Month.
Quinn Chemistry of Aqueous Marine Extracts: isolation techniques, Bioorganic Marine Chemistry, Scheuar eds., vol. 2 pp. 2–4 (1987) No Month.
Lustigman et al., Antibiotic Production by Marine Algae Isolated from the New York/New Jersey Coast, Bull. Environ. Contam. Toxicol., 46, pp. 329–335 (1991) No Month.
del Giorgio et al., Respiration Rates in Bacteria Exceed Phytoplankton Production in Unproductive Aquatic Systems, Nature, vol. 385, (1997) No Month.
Caccamese et al., Antimicrobial and Antiviral Activities of Some Marine Algae from Eastern Sicily, Botanica Marina vol. XXIV, pp. 365–367 (1981) No Month.
Capon et al., Antimicrobial Metabolites from a Pacific Sponge, Agelas sp., J. Am. Chem. Soc., 106, pp. 1819–1822 (1984) No Month.
Amade et al., Antimicrobial Activities of Marine Sponges from the Mediterranean Sea, Marine Biology, pp. 271–275 (1987) No Month.
Hornsey et al., The Production of Antimicrobial Compounds by British Marine Algae I, Brit. phycol. J. 9, pp. 353–361, (1974) No Month.
Azumi et al., Inhibitory Effect of Halocyamine, an Antimicrobial Substance from Ascidian Hemocytes, on the Growth of Fish Viruses and Marine Bacteria, Experientia, 46, pp. 1066–1068 (1990) No Month.
Burkholder, Antimicrobial Activity of Some Marine Sponges, Nature, vol. 222, pp. 983–984 (1969) No Month.
Bergquist et al., The Incidence of Antibacterial Activity in Marine Demospongiae, Systematic and Geographic Considerations, Mar. Ecol. Prog. Ser., pp. 215–221 (1978) No Month.
De Nys et al., Broad Spectrum Effects of Secondary Metabolites from the Red Alga Delisea Pulchra in Antifouling Assays, Biofouling, vol. 8, pp. 259–171 (1995) No Month.
Sreenivasa Rao et al., Antibacterial Activity of Indian Seaweed Extracts, Bontanica Marina, vo. XXIV, pp. 577–582, (1981) No Month.
Pesando et al., Screening o Marine Algae from the French Mediterranean Coast for Antibacterial and Antifungal Activity, Botanica Marina, vol. XXVII, pp. 381–386 (1984) No Month.
Nigrelli et al., Ectyonin, an Antimicrobial Agent from the Sponge, Microciona prolifer, Verrill, Zoologica, 44, pp. 173–177 (1959) No Month.
Faulkner, Interesting Aspects of Marine Natural Products Chemistry, Tretrahedron, vol. 33, pp. 1421–1443 (1977) No Month.
Walls et al., Fouling, surface bacteria and antibacterial agents of four bryozoan species found in Tasmania, Australia, J. Exp. Mar. Biol. Ecol., 169, pp. 1–13 (1993) No Month.

Becerro et al., Antimicrobial Activity and Surface Bacterial Film in Marine Sponges, J. Exp. Mar. Biol. Ecol., 179, pp. 195–205 (1994) No Month.
Hornsey et al., The Production of Antimicrobial Compounds by British Marine Algae II. Seasonal Variation in Production of Antibiotics, Br. Phycol. J. 11: 63 67, pp. 63–67, (1976) No Month.
Targett et al., Antifouling Agents Against the Benthic Marine Diatom, J. of Chemical Ecology, vol. 9, No. 7, pp. 817–829 (1983) No Month.
Bakus et al., The Use of Natural and Synthetic Toxins as Shark Repellents and Antifouling Agents, Toxicon, Suppl. 3, pp. 25–27 (1983) No Month.
D. J. Faulkner, Antibiotics From Marine Organisms, Topics in Antibiotic Chemistry, vol. 2, Sammes, ed., pp. 13–58 (1978) No Month.
D. J. Faulkner, Marine Natural Products, Natural Product Reports, vol. 3, pp. 1–33 (1986) No Month.
D. J. Faulkner, Marine Natural Products: Metabolites of Marine Algae and Herbivorous Marine Molluscs, Natural Product Reports, vol. 1, pp. 251–280 (1984(a)) No Month.
D. J. Faulkner, Marine Natural Products: Metabolites of Marine Invertebrates, Natural Product Reports, vol. 1, pp. 551–598 (1984(b)) No Month.
D. J. Faulkner, Marine Natural Products, Natural Product Reports, vol. 5 (6), pp. 613–663 (1988) No Month.
D. J. Faulkner, Marine Natural Products, Natural Product Reports, vol. 7 (4), pp. 269–309 (1990) No Month.
D. J. Faulkner, Marine Natural Products, Natural Product Reports, vol. 8 (2), pp. 97–147 (1991) No Month.
Ohta, et al., Antibiotic Substance Produced by a Newly Isolated Marine Microalga, Chlorococcum HS–101, Bull. Environ. Contam. Toxicol., vol. 50 pp. 171–178 (1993) No Month.
Targett, et al., Natural Antifoulants and Their Analogs: Applying Nature' Defense Strategies to Problems of Biofouling Control, Recent Developments in Biofouling Control, Thompson et al., eds., pp. 221–227 (1994) No Month.
Marine Biology 88, 11–21 (1985), Screening and bioassays for biologically–active substances from forty marine sponge species from San Diego, California, USA No Month.
Marine Biology 89, 1–8 (1985), Antimicrobial activity of tropical and subtropical sponges No Month.
Rao et al., "Bioactivity in Marine Algae", Bioactive Compounds From Marine Organisms, Eds. M.F. Thompson, et al., 1991 Balkema/Rotterdam, pp. 374–377. No Month.
A.B. Tadros, "The role of marine orgnanisms in fouling control", Pigment and Resin Technology, Jul. 1989, pp. 4–7.
Bakus et al., "Toxins from Marine Organisms: Studies on Antifouling", Toxins, Drugs and Pollutants in Marine Animals, Bolus et al. eds., 1984, pp. 43–46. No Month.
Nakatsu et al., "Biologically–active sterol sulfates from the marine sponge Toxadocia zumi", Experientia 39, 1983, Birkhäuser Verlag, CH–4010 Basel/Switzerland, pp. 759–761. No Month.
Chemical Abstract No. 70:80837, Dec. 1968.
Chemical Abstract No. 99:102520, 1983 No Month.
Chemical Abstract No. 102:91141, 1984 No Month.
Chemical Abstract No. 104:83795, Nov. 1985.
Chemical Abstract No. 111:235114, 1989 No Month.
Chemical Abstract No. 114:182417, 1991 No Month.
Chemical Abstract No. 119:98086, Nov. 1993.
Chemical Abstract No. 120:49991, 1993 No Month.
Chemical Abstract No. 123:108264, 1995 No Month.
Chemical Abstract No. 123:281148, 1995 No Month.

Keifer et al., "Bioactive Bromopyrrole Metabolites from the Caribbean Sponge *Agelas conifera*", J. Org. Chem. 1991, 56, pp. 2965–2975. No Month.

Sr. Alevin Mary, et al., "Bacterial–Barnacle Interaction: Potential of Using Juncellins and Antibiotics to Alter Structure of Bacterial Communities", Journal of Chemical Ecology, 19:10, 1993, pp. 2155–2167. No Month.

Iorizzi, et al., "Chemical and Biological Investigation of the Polar Constituents of the Starfish Luidia Clathrata, Collected in the Gulf of Mexico", Journal of Natural Products, 58:5, 653–671, May 1995.

R De Nys, et al., "Broad Spectrum Effects of Secondary Metabolites From The Red Alga *Delisea Pulchra* in Antifouling Assays", Biofouling, 1995, 8, pp. 259–271. No Month.

Alberts et al, "Molecular Biology of the Cell", 2nd. ed., pp. 167–168, No date.

Lackie and Dow eds., "The Dictionary of Cell Biology", 2nd ed. pp. 167 and 357, 1995 No Month.

AQUATIC ANTIFOULING COMPOSITIONS AND METHODS

This is a continuation-in-part of application Ser. No. 08/799,290 filed Feb. 13, 1997, now U.S. Pat. No. 5,695,552, which was a continuation of application Ser. No. 08/164,328 filed Dec. 9, 1993 now abandoned.

BACKGROUND OF THE INVENTION

1. Field of the Invention

This invention relates to prevention of fouling of surfaces in aquatic environments by microscopic and macroscopic organisms. More particularly, antifouling agents, compositions, coatings and methods for repelling and preventing attachment, growth and proliferation of biofouling organisms are disclosed.

2. Description of Related Art

Biofouling organisms settle on surfaces that are submerged in aquatic environments. Submerged surfaces such as water pipes, power plant water intake systems, sewer pipes, boat hulls, heat exchangers, grids, and the like are prone to biofouling. Biofouling is a major problem for most industries involved with fresh or salt water environments. Aquatic pests frequently clog pipes or become attached to submerged surfaces thus interfering with normal operations. For example, warm water associated with power plant cooling systems provides an ideal environment for the attachment and growth of aquatic organisms. Biofouling organisms also attach to other surfaces which contact aqueous solutions such as fishing nets, buoys, pilings, off-shore platforms, lumber, roofs, and concrete.

When a clean surface is introduced into an aquatic environment, it typically becomes coated with a conditioning layer of hydrophobic dissolved organic compounds. Microorganisms such as bacteria, algae, fungi, and protozoa attach to the conditioning layer and establish colonies which result in the formation of a slime layer. Such slimes can cause problems, e.g., by significantly reducing heat transfer across exchangers in cooling systems. Furthermore, slime layers contribute to the establishment of biofouling communities because planktonic (free floating) larvae of many invertebrate biofouling organisms are physically and chemically attracted to the slime layer. Examples of invertebrate biofouling organisms include mollusks such as mussels and oysters, and crustaceans such as barnacles. The release of specific compounds from the slime layer can also trigger metamorphosis of the planktonic larvae (see Hadfield (1986) Bull. Mas. Sci. 39:418–425 and Young and Mitchell, (1973) Int. Biodeterior. Bull. 9:105–109).

The blue mussel, *Mytilus edulis,* presents a particular problem at coastal power plants located in the Northeastern region of the United States. *Mytilus edulis* planktonic larvae settle on and attach to any available substratum. More recently, zebra mussels have begun to clog structures submerged in fresh water or brackish water environments. Settled juveniles grow rapidly and form dense aggregates which cause such problems as clogging inflow or outflow pipes.

Biofouling of underwater structures such as power plant water intake systems and heat exchangers results in significant economic losses to industry. Decreased fuel efficiency, increased cleaning and maintenance expenses, as well as outage expenses all contribute to increased economic expenditures. The incentive for preventing marine biofouling is great. As a result, various methods and compositions have been developed for prevention of marine biofouling. For example, utilities employ several methods for removing established biofouling communities. Periodic power outages are employed to physically enter power plant systems to remove organisms and debris. In addition, utilities often attempt to kill established biofouling communities by pumping large volumes of chlorine and molluscicides through water handling systems. However, these methods are slow acting and adversely affect the local ecology downstream from the effluent. Furthermore, these chemical treatments are inefficient because toxins are mixed in bulk water phase in an attempt to treat a surface phenomenon. Certain organisms such as the blue mussel can sense sub-lethal concentrations of some toxins and seal themselves off for long periods thereby effectively preventing contact with the toxins. Therefore, another drawback of certain existing chemical treatments is that relatively large toxic doses must be maintained for extended periods to effectively eliminate biofouling pests.

Ablative toxic antifouling coatings containing tributyl tin, copper alloys, mercury compounds, or cathodic protection have also been employed to control fouling. These antifouling coatings may include toxins which are leached into the aquatic environment to inhibit biofouling. The following examples of antifouling coatings are included for purposes of illustration. U.S. Pat. No. 5,096,488 describes a vinyl polymer or copolymer emulsion containing certain enumerated ammonium compounds. U.S. Pat. No. 5,116,407 describes an antifouling marine coating containing certain enumerated amine compounds acting as paint binders and marine biocides. U.S. Pat. No. 5,143,545 describes an antifouling marine paint containing certain enumerated water insoluble antibiotics said to be toxic to gram negative organisms of the genus Oceanospirillum, and a metallic compound, i.e., copper, tin, or zinc, acting as a marine biocide. U.S. Pat. No. 5,199,977 describes an antifouling paint containing a polymeric metal containing hybrid salt and certain enumerated organic ligands.

Observations have been made that certain sea creatures are associated with bioactive compounds. Attempts have been made to determine whether specific sponges are associated with compounds that have antimicrobial activity. Thompson et al., Marine Biology 88, 11–21 (1985), describe screening and bioassays for biologically active substances from sponge species near California, USA. Various extracts and metabolites are described as being biologically active but none of the substances was active in all assays.

A preemptive antifouling composition is needed for treating surfaces in aquatic environments which is highly effective and (1) does not contain heavy metals or synthetic toxins that adversely affect the local ecology, (2) is easy to manufacture and incorporate into or on undersea structures, (3) is easily cleaned and (4) has a prolonged effective lifetime. The benefits associated with such a composition would be enormous.

SUMMARY OF THE INVENTION

The present invention provides compounds and compositions which repel undesirable aquatic pests in an underwater environment. Aquatic organism repellents are derived from algae, tunicates, bryozoans, echinoderms and coelenterates. The present invention further provides antifouling compositions made of a carrier and an effective amount of an aquatic organism repellent derived from a creature selected from the group consisting of sponges, red algae, brown algae, green algae, tunicates, bryozoans, echinoderms and coelenterates. A method for reducing biofouling of a structure involves providing an antifouling composition as above and placing the antifouling composition in adherent contact with the structure. The present invention also provides a method of manufacturing an antifouling composition by obtaining at least one aquatic organism repellent extract from a creature selected from the group consisting of sponges, red algae, brown algae, green algae, tunicates, bryozoans, echinoderms and coelenterates, providing a carrier which is compatible with at least one of the repellents and combining the repellent extract with the carrier. The present invention further provides articles of manufacture which are resistant to biofouling which have a structure in adherent contact with an antifouling composition as described above.

A method of manufacturing an antifouling composition is provided which includes obtaining a non-polar or a semi-polar extract of at least one aquatic organism selected from the group consisting of Ulva sp., Fucus sp., Ascophyllum sp., Microciona sp., Chondrus sp., Cliona sp., Asterias sp., and Codium sp. and subjecting the non-polar or semi polar extract to at least one further purification step selected from the group consisting of high pressure liquid chromatography, vacuum liquid chromatography, low pressure liquid chromatography and thin layer chromatography.

An antifouling composition is provided which includes a repellent derived from a non-polar or semi-polar extract of at least one organism selected from the group consisting of Ulva sp., Fucus sp., Ascophyllum sp., Microciona sp. Chondrus sp. Cliona sp., Asterias sp. and Codium sp. and wherein the extract was further subjected to at least one purification step selected from the group consisting of high pressure liquid chromatography, vacuum liquid chromatography, low pressure liquid chromatography and thin layer chromatography.

An article of manufacture which is resistant to biofouling is provided including a structure incorporating an antifouling composition including a repellent derived from a non-polar or semi-polar extract of at least one organism selected from the group consisting of Ulva sp., Fucus sp., Ascophyllum sp., Microciona sp., Chondrus sp., Cliona sp., Asterias sp., and Codium sp. wherein the extract was further subjected to at least one purification step selected from the group consisting of high pressure liquid chromatography, vacuum liquid chromatography, low pressure liquid chromatography and thin layer chromatography.

A method of reducing fouling of a structure is provided including an antifouling composition including a repellent derived from a non-polar or semi-polar extract of at least one organism selected from the group consisting of Ulva sp., Fucus sp., Ascophyllum sp., Microciona sp., Chondrus sp., Cliona sp., Asterias sp., and Codium sp., wherein the extract was further subjected to at least one purification step selected from the group consisting of high pressure liquid chromatography, vacuum liquid chromatography, low pressure liquid chromatography and thin layer chromatography and placing the antifouling composition in adherent contact with the structure.

DETAILED DESCRIPTION OF THE INVENTION

In one aspect, the present invention is directed to compounds and/or extracts of creatures that live in aquatic environments that repel, prevent or otherwise deter aquatic pests from settling on or near target locations. Bioactive repellent agents according to the present invention are relatively environmentally friendly because they are biodegradable and effective in low concentrations. The repellents are naturally occurring compounds derived or extracted from underwater creatures which are "distasteful" or even toxic to underwater pests. Certain of the repellent agents possess varying degrees of hydrophobicity. As will be seen below, the hydrophobic nature of the repellents provide several advantages. Repellents according to the present invention are potent, chemically stable, relatively insoluble in water, thermally stable, and are easily harvested.

Bioactive agents (toxicants or repellents) of the present invention are derived from algae, such as Rhodophyta (red algae), Chlorophyta (green algae), Phaeophyta (brown algae), Chrysophyta (golden algae) and microalgae, and other aquatic creatures such as tunicates, sponges, coelenterates, echinoderms and bryozoans. Such bioactive agents repel or are toxic to microorganisms such as bacteria, yeast, and diatoms. The repellents are also effective against macroorganisms such as mollusks and crustaceans.

Polar, semi-polar or non polar solvents are used as the vehicles for obtaining active repellents from the above-identified creatures. The creatures are collected and then soaked in and/or blended with the solvent. Alternatively, the creatures can be homogenized in a blender in distilled water, optionally lyophilized, and then mixed with the solvent to provide an extract. Any non-polar or semi-polar solvent is suitable as long as it does not adversely react with the active repellent constituent(s) to reduce activity. Suitable solvents include ethanol, methanol, ethyl acetate, hexane, chloroform, acetonitrile and dimethylformamide.

In one embodiment, suitable creatures according to the present invention, e.g., green algae, are collected, gently cleansed, and frozen until ready for further processing. The algae is then blender homogenized in distilled water (about 1:3 weight/volume). The resulting homogenate is then lyophilized, resuspended in hexane and sonicated for about 30 minutes. The resulting mixture is then centrifuged resulting in a supernatant and a pellet. The solvent is then removed from the supernatant using a vortex vacuum evaporator. The pellet is then extracted with ethyl acetate and centrifuged. The resulting supernatant is separated from the resulting pellet. The solvent is removed from the supernatant using a vortex vacuum evaporator. The pellet is further extracted with methanol and centrifuged. Solvent is removed from the resulting supernatant using a vortex vacuum evaporator. Each extract is then tested for repellent activity as described below.

In an alternative embodiment, the collected, cleansed creatures are blended and extracted overnight by immersion in solvent, e.g., methanol (about 250 gm:200 ml) in a beaker which is shaken at about 200 rpm on a rotary shaker table. After extraction, the liquid is removed and centrifuged and the supernatant is vacuum dried to obtain a solvent extract concentrate. Tissues remaining in the beaker are air dried, e.g., in a hood, and subjected to further solvent extraction, e.g., ethyl acetate and hexane extraction by repeating the procedures of this embodiment. Each extract is then tested for repellent activity as described below.

Repellent activity is assessed by assaying for bacterial inhibition activity, mussel byssal attachment activity, bacterial anti-settlement activity, and larvae anti-settlement activity.

To perform the bacterial inhibition assay each dried extract was dissolved in about 2 ml of original solvent to get a saturated solution. About twenty to fifty (20–50) $\mu$l of each solution was added to a sterile bio-assay disc (6 mm Difco™ 1599-33) and air dried. Three disks with extract and two control disks with only solvent (all vacuum dried) were placed on a semi-solid (half usual concentration) tryptic soy agar (TSA) plate inoculated with a dilute microbial suspension. The plates were incubated for about 24 hours at room temperature. Five bacterial species (Vibrio sp., *Escherichia coli, Serratia marinarubra, Bacillus subtilis* and *Pseudomonas aeruginosa*) and a yeast (*Candida albicans*) were used in the antibiotic assay for each extract. The halo around the disks was measured and the assay was scored: highly positive (+++) if D (a zone of inhibition) was greater than 2 mm, positive (++) if D was between 1.0–2.0 mm, weakly positive if D was between 0.5–1.0 mm and no positive activity (−) if D<0.5 mm. The bacterial inhibition assay was performed on green algae, brown algae, compound ascidian, red algae, boring sponges, bryozoans and sea stars. The results are depicted in Table 1. According to K. L. Gosner, Peterson Field Guide to Atlantic Seashore, (1978) pg. 36, *F. evanescens, F. edentatus,* and *F. filiformis,* may be indistinguishable from variant vesiculosus and bladderless spirals unless "in fruit". Indeed, these 3 species are regarded by some botanists as merely ecological variants of *F. distichus*.

threads secreted by mussels avoided the sample zone. The mussel byssal thread inhibition assay was performed on green algae, brown algae, ascidian, compound ascidian, red sponge, bryozoans and sea stars. The result of the assay are depicted in Table 2.

EXAMPLES 17–31

TABLE 2

Mussel Byssal Thread Inhibition Activity

|  | Organism | Latin name | Solvent* | Mussel thread inhibition |
|---|---|---|---|---|
| 17 | Green algae | *Ulva sp.* | E.A. | H |
| 18 | Green algae | *Ulva sp.* | Met | H |
| 19 | Brown algae | *Fucus evanescens* | E.A. | P |
| 20 | Brown algae | *Fucus evanescens* | Met | P |
| 21 | Brown algae | *Ascophyllum sp.* | Met | P |
| 22 | Ascidian | *Didemnum sp.* | E.A. | P |
| 23 | Compound ascidian | — | E.A. | H |
| 24 | Red sponge | *Microciona sp.* | E.A. | P |
| 25 | Red sponge | *Microciona sp.* | Met | P |

EXAMPLES 1–16

TABLE 1

Bacterial Growth Inhibition Activity

|  | Organism | Lating name | Solvent* | Anti-bacterial activity # |  |  |  |  |  |
|---|---|---|---|---|---|---|---|---|---|
|  |  |  |  | *Vibrio sp.* | *E. coli* | *S. mari* | *C. alb* | *P. aerug.* | *B. subtilis* |
| 1 | Green algae | *Ulva sp.* | E.A. | +++ | − | ++ | − | − | ++ |
| 2 | Green algae | *Ulva sp.* | Met | +++ | − | ++ | − | − | ++ |
| 3 | Brown algae | *Fucus evanescens* | E.A. | ++ | − | − | − | − | − |
| 4 | Brown algae | *Fucus evanescens* | Met | +++ | − | − | − | − | +++ |
| 5 | Brown algae | *Fucus evanescens* | Water | +++ | − | − | − | − | +++ |
| 6 | Brown algae | *Ascophyllum sp.* | Met | +++ | − | − | − | − | ++ |
| 7 | Brown algae | *Ascophyllum sp.* | Water | +++ | − | − | − | − | +++ |
| 8 | Compound ascidian | *Didemnum sp.* | Hex | − | − | − | − | − | + |
| 9 | Compound ascidian | *Didemnum sp.* | E.A. | − | − | − | − | − | +++ |
| 10 | Compound ascidian | *Didemnum sp.* | Met | − | − | − | − | − | +++ |
| 11 | Red algae | *Chondrus sp.* | Hex | +++ | − | − | − | − | + |
| 12 | Boring (yellow) sponge | *Cliona sp.* | E.A. | ++ | − | − | − | − | ++ |
| 13 | Bryozoan | *Bugula sp.* | E.A. | − | − | − | − | − | ++ |
| 14 | Sea star | *Asterias sp.* | E.A. | + | − | − | − | − | − |
| 15 | Sea star | *Asterias sp.* | Met | + | − | − | − | − | + |
| 16 | Green algae | *Codium sp.* | E.A. | + | − | − | − | − | − |

*Met: methanol, E.A.: ethyl acetate, Hex: hexane
Highly positive (+++): D > 2 mm
Positive(++): 1 < D < 2
Weakly positive (+): 0.5 < D < 1
Negative (−): D < 0.5 mm To perform the mussel byssal thread attachment assay, juvenile blue mussels, *Mytilus edulis,* were collected from tidal rocks and maintained in an aquarium with seawater at 18° C. on a diet of the microalga, *Isochrysis galbana* (a haptophyte) until needed. Frosted slides (3×1') were washed with methanol and dried before use. The sample zone was coated with a test extract which was re-dissolved in its solvent as above. After the solvent was completely evaporated, two juvenile mussels (about 1–2 cm in shell length) were fixed around the edge of the sample zone using a commercial super glue (Duro™). The bioassay slides prepared in this way were placed at the bottom of an aquarium with running sea water. The turnover time of the seawater was set to be about 1 hour for the first 12 hours to minimize the contamination of seawater by the extract. The mussels tried to attach themselves on the slide using many byssal threads. If an extract was bioactive, most byssal TABLE 2-continued Mussel Byssal Thread Inhibition Activity

|  | Organism | Latin name | Solvent* | Mussel thread inhibition |
|---|---|---|---|---|
| 26 | Boring (yellow) sponge | *Cliona sp.* | E.A. | P |
| 27 | Boring (yellow) sponge | *Cliona sp.* | Met | P |
| 28 | Bryozoan | *Bugula sp.* | E.A. | P |
| 29 | Sea star | *Asterias sp.* | E.A. | P |
| 30 | Green algae | *Codium sp.* | E.A. | P |
| 31 | Green algae | *Codium sp.* | Met | H |

*Met: methanol, E.A.: ethyl acetate, Hex: hexane
Highly positive inhibition (H)
Positive inhibition (P)

To perform the bacterial anti-settlement assay, a total of about 0.5 ml extract was spread onto the frosted portion of six glass slides and the solvent was evaporated. An equal number of control slides was treated with pure solvent in an identical manner. Each slide was placed into a 50 ml Falcon tube filled with approximately $10^6$ cells·ml$^{-1}$ of *Pseudomonas aeruginosa*. Log-phase cells were used because growth status of the bacterial can affect their attachment significantly. The tubes were capped and placed horizontally onto a rotary shaker so that the treated surfaces faced downward.

Tubes were removed randomly from the tray at time intervals of about 1–2 hours. Slides were slowly immersed in about 2% formaldehyde to remove excess water as well as fixing the bacteria. About thirty microliters of a fluorescent stain (DAPI) was added, the cover slip dropped and the number of attached bacteria counted in 20 fields on an epifluorescent microscope. The bacterial anti-settlement assay was performed on green algae, brown algae, ascidian, red algae and bryozoans. The results of the assay are depicted in Table 3.

EXAMPLES 32–38

TABLE 3

Bacterial Anti-Settling Activity

| | Organism | Latin name | Solvent* | Bassel anti-settling *P. aeruginosa* | activity# *E. coli* |
|---|---|---|---|---|---|
| 32 | Green algae | Ulva sp. | E.A. | H | — |
| 33 | Brown algae | Fucus evanescens | E.A. | H | H |
| 34 | Brown algae | Fucus evanescens | Met | H | — |
| 35 | Brown algae | Ascophyllum sp. | Met | H | H |
| 36 | Ascidian | Didemnum sp. | Met | P | — |
| 37 | Red algae | Chondrus sp. | Hex | P | — |
| 38 | Bryozoan | Bugula sp. | Met | — | H |

*Met: methanol, E.A.: ethyl acetate, Hex: hexane
Highly positive inhibition (H)
Positive inhibition (P)

To perform coated slide larval anti-settlement assay, pre-settling mussel and oyster larvae with shell length of about 250–300 μm were used and stored at 8° C. The tested extract was coated on frosted glass and air dried. Coated and clean (control) slides were placed in an aquarium with flowing seawater. The turnover time of the seawater is set to be about 1 hour for the first 12 hours to minimize the contamination due to the extract. *I. galbana* diet is added into the aquarium with flowing seawater. Larval density was 2 larvae ml$^{-1}$. The container was aerated with two air stones. Tested slides and control slides were removed and the number of larvae settled on them was calculated and compared. The larval anti-settlement assay was performed on green algae, boring sponges and brown algae. The results of the assay are depicted in Table 4.

EXAMPLES 39–41

TABLE 4

Mussel and Oyster Larval Settlement Inhibition

| | Organism | Latin name | Solvent* | Larval settlement inhibition |
|---|---|---|---|---|
| 39 | Green algae | Codium sp. | E.A. | P |
| 40 | Boring (yellow) sponges | Cliona sp. | Met | P |
| 41 | Brown algae | Fucus evanescens | Met | P |

*Met: methanol, E.A.: ethyl acetate, Hex: hexane
Positive inhibition (P)

In another aspect of the present invention, the extracts above are subjected to further purification steps. Techniques involving high pressure liquid chromatography (HPLC), vacuum liquid chromatography (VLC) and thin layer chromatography (TLC) are useful. For example, a large volume of methanol extract from *F. evanescens* was evaporated to dryness and then redissolved in 1 ml of 100% methanol to provide a concentrate. The concentrate was refrigerated overnight and an inactive water soluble precipitate formed from the solution which was removed by decanting. The decanted mixture was then subjected to high pressure liquid chromatography (HPLC) using a C18 reverse phase column and gradient or isocratic elutions. Isocratic elutions with 33% methanol were found to yield a fraction with strong antimicrobial properties. Separations were not improved using methanol/water gradient elutions.

Vacuum liquid chromatographic (VLC) techniques are also useful herein. Indeed, certain non-bioactive materials are removed by sequential elutions of *F. evanescens* methanol extracts or *Ulva lactuca* ethyl acetate extracts on a preparatory C18 reverse phase column. Separation into fractions is accomplished by eluting with solvent having sequentially decreasing polarity. Such solvents include 100% water, 3:1 water: MeOH, 1:3 water:MeOH, 100% MeOH, 3:1 MeOH: EA, 1:1 MeOH:EA, 1:3 MeOH:EA, 100% EA (MeOH=methanol; EA=ethyl acetate). Thin layer chromatography (TLC) may be used as a vehicle to determine which solvents are useful in chromatographic techniques herein. Resulting fractions are then tested using antimicrobial assays. With regard to *Ulva lactuca*, as the polarity of the mobile phase decreased, more bioactive material eluted. A solvent mixture of methanol:ethyl acetate 1:3 yielded a fraction having the highest bioactivity.

Similarly, a methanol extract of *A. nodosum* was purified using sequential VLC by eluting with solvents of decreasing polarity. Such solvents include 100% water, 3:1 water: MeOH, 1:3 water:MeOH, 100% MeOH, 3:1 MeOH: EA, 1:1 MeOH:EA, 1:3 MeOH:EA, 100% EA More bioactive material was recovered from three of the less polar mobile phases (100% MeOH, 1:3 MeOH:EA, 100% EA).

Low pressure liquid chromatography (LPLC) techniques are also useful herein. For example, Sephadex LH-20, a liquid chromotography solid phase porous medium designed for molecular sizing of organic materials is swelled overnight in 95% methanol and packed into an LPLC column (1.5×30 cm). Then, e.g., ethyl acetate extract of *U. lactuca* is added to the column. Aliquots (about 30 ml) of a solvent, e.g., methanol, 2-propanol or the like, as the isocratic phase are repetitively run through the column to obtain a series of eluents. Thus, LPLC can be used before HPLC techniques for rapid separation of an active fraction from a crude extract.

The following non-limiting example illustrates a purification process according to the present invention.

EXAMPLE 42

Three marine algae, *U. lactuca, A. nodosum*, and *F. evanescens* were collected from intertidal waters during spring and early summer. Three types of crude extract, methanol (MeOH), ethyl acetate (EA), and hexane-soluble, were prepared from each organism. Each frozen or freshly-collected organism was blended or macerated and then soaked overnight in MeOH in a covered beaker on a rotary shaker table. After extraction, the solvent was removed and centrifuged and the supernatant was vacuum evaporated to obtain the MeOH crude extract concentrate. Tissues remaining in the beakers were air dried and subjected to EA and hexane extraction by repeating the procedures above. From a preliminary screening, EA extract from *U. lactuca* and MeOH extracts from *A. nodosum* and *F. evanescens*, exhibited strong antimicrobial activity. These extracts were subjected to further purification as follows.

Thin layer chromatography (TLC) and vacuum liquid chromatography (VLC) were used to further purify the bioactive extracts. Analytical TLC was employed to obtain guidelines for VLC separations. To perform TLC separations, crude extracts were spotted onto Whatman silica gel plates (reverse phase, 20×5 cm) and developed in high purity or solvent mixtures of varying polar strengths (100% water, 1:1 water:MeOH, 1:3 water:MeOH, 100% MeOH) (Gerhart et al., J. Chem. Ecol. 14(10) pp. 1905–1915 (1988); Sears et al., J. Chem. Ecol. 16(3) pp. 791–799 (1990)). Migration of materials was observed using a UV lamp.

According to band patterns under different mobile phases, the appropriate mobile phase for purifying a crude extract was determined and used in VLC separations to obtain higher yields of semi-purified extract rapidly. Seven grams of packing material (Sorbsil $C_{18}$) were loaded to a Kontes 1.5×15 column and the VLC system was set up according to Coll et al., J. Nat. Prod. 49(5) pp. 934–936 (1986). With this system, extracts were eluted with solvents of decreasing polarity. For the purification of MeOH extract from *F. evanescens*, the column was conditioned with 40 ml of 95% MeOH. The crude extract (0.5 ml) was pipetted into the column. The crude extract was repetitively eluted with 30 ml of MeOH, which produced three bands of distinct color: brown, yellow, and green. Each band was collected, accumulated from repetitive runs and subjected to antimicrobial assays. The MeOH extract from *A. nodosum* and EA extract from *U. lactuca* were purified by sequentially eluting with 1) 100% water, 2) water: MEOH=3:1, 3) water:MeOH=1:3, 4) 100% MeOH, 5) MeOH:EA=3:1, 6) MeOH:EA=1:1, 7) MeOH:EA=1:3 and 8)100% EA. Each fraction was collected, accumulated and subjected to antimicrobial assays.

Each fraction accumulated from the 3 elutions was completely impregnated into a separate bioassay disk so that the dosage/disk (see Tables 5–7) represents the relative yield of each fraction derived from the crude extract. Marine microorganisms were isolated from (i) living organism (e.g., algae, ascidian); (ii) non-living surfaces (stones, experimental plates); and (iii) surrounding seawater to create a culture collection for screening bioactivity of extracts. A suspension of isolated microorganisms was seeded uniformly over the surface of a half strength marine agar (2216) plate. Three dried sample disks and two solvent control disks without absorbed extract were placed on the agar plate. Plates were examined for bacterial growth after 24 h incubations at room temperature. If an extract has no effect on bacterial metabolism, they grow in close proximity to the paper disk. If however, the extract has an inhibitory effect on the bacteria, a zone of no growth is observed around the paper disk (Uriz et al., Marine Biology, 113, pp. 287–297 (1992).

The antimicrobial activity and inhibition zone for the 8 fractions from *U. lactuca* is shown in Table 5. Fractions 1 to 4 did not produce any inhibitory effects at all. Fraction 6 produced the widest antimicrobial spectrum. The fifth, seventh, and last fractions inhibit a portion of the isolates inhibited by fraction 6 (25–67%). Only two of the isolates (MSCC 3 and 5) which were inhibited by the crude extracts were not inhibited by any fraction of semi-purified extracts (Table 5), suggesting synergistic interactions of multiple constituents.

TABLE 5

Width of inhibition zone (mm) produced by each fraction from VLC separation of EA extract from Ulva lactuca

| Microorganisms | Fraction 1 2.95 (ug/disk) | 2 2.72 | 3 3.86 | 4 | 5 7.2 | 6 18.1 | 7 15.1 | 8 11.7 |
|---|---|---|---|---|---|---|---|---|
| MSCC3 | — | — | — | — | — | — | — | — |
| MSCC5 | — | — | — | — | — | — | — | — |
| MSCC13 | — | — | — | — | — | 6 | 2 | — |
| MSCC17 | — | — | — | — | — | 6 | 5 | 2 |
| MSCC18 | — | — | — | — | — | 2 | — | — |
| MSCC23 | — | — | — | — | 2 | 1 | — | — |
| MSCC24 | — | — | — | — | 2 | 2 | — | — |
| MSCC25 | — | — | — | — | — | — | — | — |
| MSCC26 | — | — | — | — | — | — | — | — |
| MSCC27 | — | — | — | — | — | 0.8 | 1.8 | — |
| MSCC28 | — | — | — | — | — | — | — | — |
| MSCC30 | — | — | — | — | — | 3 | 1.5 | — |
| MSCC31 | — | — | — | — | — | — | — | — |
| MSCC32 | — | — | — | — | — | — | — | — |
| MSCC33 | — | — | — | — | — | 1.5 | 2 | — |
| MSCC34 | — | — | — | — | — | — | — | — |
| MSCC35 | — | — | — | — | — | — | — | — |
| MSCC36 | — | — | — | — | — | 1.5 | 1.5 | — |
| MSCC37 | — | — | — | — | — | — | — | — |

TABLE 5-continued

Width of inhibition zone (mm) produced by each fraction from VLC separation of EA extract from Ulva lactuca

| Microorganisms | Fraction 1 2.95 (ug/disk) | 2 2.72 | 3 3.86 | 4 — | 5 7.2 | 6 18.1 | 7 15.1 | 8 11.7 |
|---|---|---|---|---|---|---|---|---|
| MSCC38 | — | — | — | — | — | — | — | — |
| Vibrio | — | — | — | — | — | 4 | 2 | 2 |
| B. subtilis | — | — | — | — | — | — | — | — |
| S. aureus | — | — | — | — | — | 1 | 1.5 | 3 |
| E. coli 25922 | — | — | — | — | — | — | — | — |
| E. coli (F + Strain) | — | — | — | — | — | — | — | — |
| E. faecalis | — | — | — | — | 1 | 1 | — | — |
| E. faecium | — | — | — | — | — | — | — | — |
| P. aeroginosa | — | — | — | — | — | — | — | — |

Fractions 1–8 are the eluents in the following mobile phases 100% water, 3:1 water:MeOH, 1:3 water:MeOH, 100% MeOH, 3:1 MeOH:EA, 1:1 MeOH:EA, 1:3 MeOH:EA, and 100% EA, respectively.

The pattern of antimicrobial activity for purified fractions of *A. nodosum* appears to be different from that of *U. lactuca*. The first three factions eluted in (eluted in H$_2$O, H$_2$O:MeOH=3:1, and H$_2$O:MeOH=1:3) and the last fraction (eluted in 100% EA) had no effect on any bacteria (Table 6). From the results of antimicrobial spectra of fractions 4 to 7, which showed antimicrobial activity against one or more strains, it is apparent that there exist two constituents with quite different antimicrobial specificity. Fraction 4 appeared to contain a bioactive compound with extremely potent inhibitory effect on a unique set of isolates (MSCC 18, 30, 33, 37 and *E. coli* 25922). However, fraction 4 had no inhibitory effect on another set of isolates (MSCC 17, 24, Vibrio sp.), which were strongly inhibited by fractions 6 and 7. The antimicrobial activity of fractions 6 and 7 appeared to come from the same bioactive compound since both displayed inhibitory effect against exactly the same set of isolates (MSCC17, 24, 30 and Vibrio sp.). This bioactive constituent did not have any inhibitory effect on MSCC 18, 33, 37 and *E. coli* 25922 (which are strongly inhibited by fraction 4) at higher dosage (Table 6). Some isolates (e.g., MSCC3–6, 25, 28, 32, 36) which were inhibited by the crude extracts were not inhibited by any fraction of semi-purified extracts, again suggesting synergistic interactions.

TABLE 6

Width of inhibition zone (mm) produced by each fraction from VLC separation of MeOH extract from *A. nodosum*

| Microorganisms | Fraction 1 57.3(ug/disk) | 2 76 | 3 76 | 4 51 | 5 177 | 6 142 | 7 198 | 8 77 |
|---|---|---|---|---|---|---|---|---|
| MSCC3 | — | — | — | — | — | — | — | — |
| MSCC4 | — | — | — | — | — | — | — | — |
| MSCC5 | — | — | — | — | — | — | — | — |
| MSCC6 | — | — | — | — | — | — | — | — |
| MSCC8 | — | — | — | — | — | — | — | — |
| MSCC10 | — | — | — | — | — | — | — | — |
| MSCC17 | — | — | — | — | 2 | 3 | 2 | — |
| MSCC18 | — | — | — | 10 | — | — | — | — |
| MSCC24 | — | — | — | — | — | 1 | 2 | — |
| MSCC25 | — | — | — | — | — | — | — | — |
| MSCC26 | — | — | — | — | — | — | — | — |
| MSCC28 | — | — | — | — | — | — | — | — |
| MSCC30 | — | — | — | 10 | — | 1 | 0.5 | — |
| MSCC32 | — | — | — | — | — | — | — | — |
| MSCC33 | — | — | — | 8 | — | — | — | — |
| MSCC36 | — | — | — | — | — | — | — | — |
| MSCC37 | — | — | — | 7 | — | — | — | — |
| MSCC38 | — | — | — | — | — | — | — | — |

TABLE 6-continued

Width of inhibition zone (mm) produced by each fraction from VLC separation of MeOH extract from *A. nodosum*

| Microorganisms | Fraction 1 57.3(ug/disk) | 2 76 | 3 76 | 4 51 | 5 177 | 6 142 | 7 198 | 8 77 |
|---|---|---|---|---|---|---|---|---|
| Vibrio sp. | — | — | — | — | — | 2 | 0.5 | — |
| B. subtilis | — | — | — | — | — | — | — | — |
| S. aureus | — | — | — | — | — | — | — | — |
| Escherichia coli 25922 | — | — | — | 4 | — | — | — | — |
| E. faecalis | — | — | — | — | — | — | — | — |
| E. faecium | — | — | — | — | — | — | — | — |

Fractions defined in Table 5

The pattern of antimicrobial spectrum for the purified fractions of *F. evanescens* is similar to that of *A. nodosum* (Table 6) in that there is evidence that more than one bioactive compound exists. The first fraction (brown) from *F. evanescens* was found to possess potent antimicrobial activity against Vibrio sp. (Gram−) but had no effect on *B. subtilis* (Gram+) (Table 7). However, the green extract from *F. evanescens* was found to possess potent antimicrobial activity against *B. subtilis* but had no effect on Vibrio sp. Because the cruder extract showed clear antimicrobial activity against both *B. subtilis* and Vibrio sp., it is evident that the two further purified extracts contain at least two distinct antimicrobial metabolites. Again it was found that some isolates (e.g., MSCC 32–33, 38) which were inhibited by the cruder extracts were not inhibited by any fraction of further purified extracts.

TABLE 7

Width of inhibition zone (mm) produced by each fraction from VLC separation of MeOH extract from *F. evanescens*

| Microorganisms | Fraction 1 157(g/disk) | 2 79.9 | 3 331 |
|---|---|---|---|
| MSCC2 | — | — | — |
| MSCC17 | 3 | 1 | — |
| MSCC27 | 3 | — | — |
| MSCC18 | 2 | 2 | — |
| MSCC32 | — | — | — |
| MSCC33 | — | — | — |
| MSCC37 | 2 | — | — |
| MSCC38 | — | — | — |
| Vibrio sp. | 2 | — | — |

TABLE 7-continued

Width of inhibition zone (mm) produced by each fraction
from VLC separation of MeOH extract from *F. evanescens*

| Microorganisms | Fraction 1 157(g/disk) | 2 79.9 | 3 331 |
|---|---|---|---|
| B. subtilis | — | — | 2.5 |
| S. aureaus | 4 | 1 | — |
| E. faecalis | — | — | — |
| E. faecium | — | — | — |
| P. aeruginosa | — | — | — |

According to the present invention, the aquatic pest repellents are incorporated into an acceptable carrier or vehicle to deliver repellent activity to desired target sites. The hydrophobic nature of the active constituents is advantageous in certain instances because such constituents are not freely dissolved and/or diluted in aqueous environments and are thus adapted to be maintained at the desired location by various immobilization techniques.

Thus, in another aspect, the present invention provides compositions which reduce or completely eliminate fouling of underwater structures by aquatic pests. The compositions include a carrier which contains at least one of the above-described antifouling agents that repel, prevent or otherwise deter aquatic pests from settling on structures incorporating the compositions. In accordance with one aspect of the present invention, the unique combination of carrier and antifouling agent augment one another by creating a slippery surface which causes problems for organisms attempting to anchor on the surface and, further, a chemically hostile local environment that the organisms find "distasteful" and in some cases toxic. Antifouling agents or repellents according to the present invention are bioactive compounds derived from natural sources that upon entry into the ecosystem are biodegradable and environmentally friendly.

Repellents according to the present invention can be incorporated into structural members to provide aquatic pest repellent structures which are intended to be placed in aquatic environments. In this manner, the structure itself has integral aquatic pest repellency. The inventive antifouling agents can also be incorporated into surface coatings of structures intended for underwater use. Materials which can incorporate the antifouling agents are known and must be compatible with the repellents, i.e., there is no interaction between the materials and the repellents which degrades or is otherwise detrimental to the repellent activity of the antifouling agents.

Vehicles (a structure or coating) which contain one or more repellent agents provide a medium which allow the bioactive compounds to exert repellent activity in the locus to be protected over a period of time either by sustained release of the agent(s) or by creating a fixed effective surface concentration of the agent.

Diffusional systems are well suited to release the repellent agents to target areas. Diffusional systems include reservoir devices in which a core of repellent is surrounded by a porous membrane or layer, or matrix devices in which the repellent is distributed throughout an inert matrix. Materials which may be used to form reservoirs or matrices include silicones, methacrylates, vinyl compounds such as polyvinyl chloride, olefins such as polyethylene or polypropylene, fluoropolymers such as polytetrafluoroethylene and polyesters such as terephthalates. The diffusional systems may be molded into a film or other layer material which is then placed in adherent contact with the structure intended for underwater use. Alternatively, the repellent agent may be mixed with a resin, e.g., polyvinyl chloride and then molded into a desired shape, e.g., a pipe, which integrally incorporates the repellent to form a structure having inherent fixed repellency. Increasing the concentration of fixed repellent at or near the surface allows increased efficacy. Alternatively, the entire structural member may be a porous matrix which allows diffusion of the repellent into the surrounding environment.

In a preferred embodiment, crude or purified extracts herein are dissolved or diluted in solvent such as methanol, ethyl acetate, hexane, chloroform, acetonitrile, dimethylformamide. Porous or semi-porous polyvinyl chloride structures such as pipes, walls, plates, etc. are immersed and soaked in one or more bioactive antifouling solutions herein to load the structure with repellent. Air pockets in the PVC structure retain the repellent and act as a reservoir for repellent. Any porous or semi-porous solid or semi-solid polymeric material capable of withstanding the marine environment is suitable for loading in this manner. Optionally, a structure loaded with repellent can be coated with a layer of material which affects diffusion of the repellent from the structure. Permeable layers may be formed by spraying or painting the surfaces of loaded structures with, e.g., polymer forming materials which are well-known in the art. As a general principal, the thicker the coating the greater the amount of inhibition of diffusion. Any technique known to those with skill in the art of applying a layer which allows and/or affects diffusion of repellent from the structure may be used herein. Examples of certain materials suitable for forming layers are provided below.

Repellents according to the present invention may be applied as surface coatings which are corrosion resistant and applied by painting or otherwise bonding or adhering a liquid or paste-like composition containing the repellent to the material intended for underwater use. After applying the liquid or paste coating, it hardens to form a repellent coating. The coatings may be applied in a variety of ways which are known in the art. Mastic coatings, polymerizable compositions, or solvent-based paints which contain one or more repellents can be applied to structures intended for underwater use.

For example, a loaded or unloaded structure may be coated with a repellent solution and allowed to dry. A diffusion affecting coating layer is then applied by, e.g., painting or spraying over the dried extract. This layering process may be repeated multiple times to provide a prolonged or sustained release vehicle for repellency. The repellent may also be incorporated directly into the diffusion affecting coating layers. In a preferred embodiment, the structure is loaded with repellent and then coated as described above. It is also noted that porous or semi-porous structures provide a more secure surface for "slippery" coating materials since the coating material partially enters the interstitial spaces of the structure and polymerizes therein which helps anchor the coating to the surface.

Materials which may be used as coating vehicles include phenolic resins, silicone polymers, chlorinated rubbers, coal tar and epoxy combinations, epoxy resin cured from a solvent solution with polyfunctional amines, polyamide resins, vinyl resins in solvent solutions, elastomers, fluoropolymers, polyesters and polyurethanes. Especially preferred vehicles for the repellent agents of the present invention are silicone polymers. Silicone resins, silicone RTV polymers, and silicone heat cured rubbers are suitable and are described in the Encyclopedia of Polymer Science and Engineering, Vol. 15, pp. 204 et seq. (1989) hereby incorporated by reference. Polydimethyl siloxanes are very well suited as a vehicle for containing the inventive repellents. These compositions create a slippery surface that, as was discussed above, augments the chemical repellent activity of the repellent agents. Coating compositions used herein include EXTRUDE™ polyvinylsiloxane composition commercially available from Kerr Manufacturing Company, Romulus, Mich.; a vinylpolydimethylsiloxane composition (EXSIL2205-DI) commercially available from GE Silicones, Waterford, N.Y.; and a dimethyl polysiloxane composition (EXSIL2200-D1) commercially available from GE Silicones, Waterford, N.Y.

Microencapsulation techniques are useful in maintaining sustained focal release of repellents according to the present invention. Microencapsulation may also be used for providing improved stability of the antifouling composition. The active agents of the present invention may be microencapsulated in structures in the form of spheres, aggregates of core material embedded in a continuum of wall material, capillary designs or incorporated into films and paints. The core material of a microcapsule containing a repellent agent may be in the form of a liquid droplet, an emulsion, a suspension of solids, a solid particle, or a crystal. The microcapsule coating material may be an organic polymer, hydrocolloid, wax, fat, lipid, metal, or inorganic oxide. Silicone polymers are the most preferred microcapsule coating material for use with the present invention. Microencapsulation techniques are well known in the art and are described in the Encyclopedia of Polymer Science and Engineering, Vol. 9, pp. 724 et seq. (1989) hereby incorporated by reference.

The bioactive repellent in association with an acceptable carrier may be applied to submersible or submerged surfaces such as water intake systems, water cooling tubes, heat exchangers, and any other surfaces which are subject to biofouling. For example, the composition may be employed as an antifouling composition for boat hulls, fishing netting, buoys, pilings, lumber, roofs, and concrete. Dipping, spraying, brushing and laminating are other means for applying the antifouling composition. Furthermore, the novel antifouling composition may be used for removing microorganisms from surfaces in hospitals or other surfaces where an aseptic environment is desirable.

The following non-limiting example illustrates a coating embodiment according to the present invention.

EXAMPLE 43

Coated settling plates were exposed to marine and freshwater biofoulers in Port Jefferson Harbor, Long Island, N.Y. and Oneida Lake at the Cornell Biological Field Station. Settling plates ("4.4×4.5", expanded PVC) were cleaned with 100% ethanol and four equal areas were marked by pencil. One quarter of each plate was impregnated with semi-purified extract and then painted by brush with EXTRUDE™ (Kerr Manufacturing). The second quarter was impregnated with extract only (without EXTRUDE™ coating). The third quarter was painted with EXTRUDE™ only (coating control) and the fourth quarter was left barren (plain surface control). A total of 14 plates, 7 plates for Fucus extract and another 7 plates for Ulva extracts were prepared for the deployment. The settling plates were held in a rack (AQUARACK™, AquaTach Environmental, Inc.) and exposed for 1, 2, 4, 8, 30, 60 and 90 days and sacrificed for laboratory examination. Two test plates, one coated with Fucus extract and another with Ulva extract, were returned to the lab in particle-free seawater (0.2 $\mu$m filter-sterilized and then autoclaved) at each time point. Macrofouling communities were enumerated on all surfaces and a 4 $cm^2$ area was cut from each quarter of the plate.

In estuarine field trials (Pt. Jefferson Harbor) over two month exposures, portions of settling plates covered with composite coating (silicone and algal extract) experienced 5–10 times less cumulative fouling than uncoated portions or portions coated with silicone polymers alone. Low rates of *D. polymorpha* recruitment generally were observed in Oneida lake. The highest settling density of zebra mussels observed on the control plates was the equivalent of 1,200 individuals $m^2$. Similar to the marine deployments, portions of settling plates covered with hybrid coatings were completely devoid of *D. polymorpha;* whereas uncoated portions of the same plates attracted these foulers in significant numbers. By day 70, portions coated with extract only exhibited modest recruitment, perhaps due to surface depletion of the bioactive substance.

In the lake field trials, macroscopic surface colonization was dominated by a species of Ostracoda ($\leq$52,000 individuals $m^2$). These micro-crustaceans also produce planktonic larvae that settle onto surfaces and compete with zebra mussels for space and resources. Like zebra mussels, they were never observed attached to quadrants with coating containing repellent. However, they appeared to attach more to the inert silicone coating than the untreated PVC plate surfaces.

The examples and embodiments depicted in this specification are not intended to be limitations on the inventive concept described herein. Accordingly, one with skill in the art may make modifications in the methods and products which are intended to be covered by the following claims.

What is claimed is:

1. A method of manufacturing an antifouling composition comprising obtaining a non-polar or a semi-polar extract of at least one aquatic organism selected from the group consisting of Ulva sp., Fucus sp., Ascophyllum sp., Microciona sp., Chondrus sp., Cliona sp., Asterias sp., and Codium sp. and subjecting the non-polar or semi polar extract to at least one further purification step selected from the group consisting of high pressure liquid chromatography, vacuum liquid chromatography, low pressure liquid chromatography and thin layer chromatography.

2. A method of manufacturing an antifouling composition according to claim 1, wherein the non-polar or semi-polar extract is obtained using a solvent selected from the group consisting of methanol, ethyl acetate and hexane.

3. A method according to claim 1, wherein Ulva sp. is *Ulva lactuca,* Fucus sp. is *Fucus evanescens* and Ascophyllum sp. is *Ascophyllum nodosum.*

4. A method according to claim 3, wherein a ethyl acetate extract of *U. lactula* is subjected to vacuum liquid chromatography.

5. A method according to claim 3, wherein a methanol extract of *A. nodosum* or *F. evanescens* is subjected to vacuum liquid chromatography.

6. An antifouling composition comprising a repellent derived from a non-polar or semi-polar extract of at least one organism selected from the group consisting of Ulva sp., Fucus sp., Ascophyllum sp., Microciona sp., Chondrus sp., Cliona sp., Asterias sp., and Codium sp., wherein the repellant was obtained by subjecting the extract to at least one purification step selected from the group consisting of high pressure liquid chromatography, vacuum liquid chromatography, low pressure liquid chromatography and thin layer chromatography.

7. An antifouling composition according to claim 6, wherein the non-polar or semi-polar extract is obtained using a solvent selected from the group consisting of methanol, ethyl acetate and hexane.

8. An antifouling composition according to claim 6, wherein Ulva sp. is *Ulva lactuca,* Fucus sp. is *Fucus evanescens* and Ascophyllum sp. is *Ascophyllum nodosum.*

9. An antifouling composition according to claim 8, wherein an ethyl acetate extract of *U. lactula* is subjected to vacuum liquid chromatography.

10. An antifouling composition according to claim 8, wherein a methanol extract of *A. nodosum* or *F. evanescens* is subjected to vacuum liquid chromatography.

11. An article of manufacture which is resistant to biofouling comprising a structure incorporating an antifouling composition including a repellant derived from a non-polar or semi-polar extract of at least one organism selected from the group consisting of Ulva sp., Fucus sp., Ascophyllum sp., Microciona sp., Chondrus sp., Cliona sp., Asterias sp., and Codium sp., wherein the repellant was obtained by subjecting the extract to at least one purification step selected from the group consisting of high pressure liquid chromatography, vacuum liquid chromatography, low pressure liquid chromatography and thin layer chromatography.

12. An article of manufacture which is resistant to biofouling according to claim 11 wherein the non-polar or semi-polar extract is obtained using a solvent selected from the group consisting of methanol, ethyl acetate and hexane.

13. An article of manufacture which is resistant to biofouling according to claim 11, wherein Ulva sp. is *Ulva lactuca,* Fucas sp. is *Fucas evanescens* and Ascophyllum sp. is *Ascophyllum nodosum.*

14. An article of manufacture which is resistant to biofouling according to claim 13, wherein a ethyl acetate extract of *U. lactula* is subjected to vacuum liquid chromatography.

15. An article of manufacture which is resistant to biofouling according to claim 13, wherein a methanol extract of *A. nodosum* or *F. evanescens* is subjected to vacuum liquid chromatography.

16. A method of reducing fouling of a structure comprising providing an antifouling composition including a repellant derived from a non-polar or semi-polar extract of at least one organism selected from the group consisting of Ulva sp., Fucus sp., Ascophyllum sp., Microciona sp., Chondrus sp., Cliona sp., Asterias sp., and Codium sp., wherein the repellant was obtained by subjecting the extract to at least one purification step selected from the group consisting of high pressure liquid chromatography, vacuum liquid chromatography, low pressure liquid chromatography and thin layer chromatography and placing the antifouling composition in adherent contact with the structure.

17. A method of reducing fouling of a structure according to claim 16, wherein the non-polar or semi-polar extract is obtained using a solvent selected from the group consisting of methanol, ethyl acetate and hexane.

18. A method of reducing fouling of a structure according to claim 16, wherein Ulva sp. is *Ulva lactuca,* Fucus sp. is *Fucus evanescens* and Ascophyllum sp. is *Ascophyllum nodosum.*

19. A method of reducing fouling of a structure according to claim 18, wherein a ethyl acetate extract of *U. lactula* is subjected to vacuum liquid chromatography.

20. A method of reducing fouling of a structure according to claim 18, wherein a methanol extract of *A. nodosum* or *F. evanescens* is subjected to vacuum liquid chromatography.

\* \* \* \* \*